US012788905B2

(12) United States Patent
Tseng

(10) Patent No.: US 12,788,905 B2
(45) Date of Patent: Nov. 10, 2026

(54) MULTIFUNCTIONAL WEARING DEVICE

(71) Applicant: Yu-Jen Tseng, Taipei City (TW)

(72) Inventor: Yu-Jen Tseng, Taipei City (TW)

( * ) Notice: Subject to any disclaimer, the term of this patent is extended or adjusted under 35 U.S.C. 154(b) by 428 days.

(21) Appl. No.: 18/592,479

(22) Filed: Feb. 29, 2024

(65) Prior Publication Data

US 2024/0293630 A1 Sep. 5, 2024

(30) Foreign Application Priority Data

Mar. 1, 2023 (TW) ................................ 112107334

(51) Int. Cl.

*A61M 11/04* (2006.01)
*A61F 7/00* (2006.01)
*A61M 11/00* (2006.01)
*A61N 5/06* (2006.01)
*G02C 11/00* (2006.01)

(52) U.S. Cl.

CPC ......... *A61M 11/042* (2014.02); *A61F 7/0085* (2013.01); *A61M 11/005* (2013.01); *A61N 5/0613* (2013.01); *G02C 11/00* (2013.01); *A61F 2007/0004* (2013.01); *A61F 2007/0055* (2013.01); *A61F 2007/0075* (2013.01); *A61F 2007/0086* (2013.01); *A61M 2205/3306* (2013.01); *A61M 2205/3368* (2013.01); *A61M 2205/3606* (2013.01); *A61M 2205/3646* (2013.01); *A61M 2209/088* (2013.01); *A61M 2210/0612* (2013.01); *A61M 2230/20* (2013.01); *A61M 2230/50* (2013.01); *A61N 2005/0648* (2013.01); *A61N 2005/0652* (2013.01); *A61N 2005/0663* (2013.01)

(58) Field of Classification Search

CPC ....... A61F 9/0008; G02C 11/00; G02C 5/001; G02C 11/02; G02C 5/00; G02C 5/14; G02C 7/02

See application file for complete search history.

(56) References Cited

U.S. PATENT DOCUMENTS

| | | | | |
|---|---|---|---|---|
| 5,013,145 A * | 5/1991 | Croll | ........................ | G02C 7/02 351/158 |
| 8,770,743 B2 * | 7/2014 | Tsubota | ................ | G02C 5/001 351/158 |
| 2012/0162598 A1 * | 6/2012 | Tsubota | ................ | G02C 11/00 351/158 |

* cited by examiner

*Primary Examiner* — Jon C Morales

(74) *Attorney, Agent, or Firm* — CKC & Partners Co., LLC

(57) ABSTRACT

The present disclosure is related to a multifunctional wearing device. The multifunctional wearing device includes a spectacle frame, a light-transmitting container, a liquid storage chamber and an oscillator. The light-transmitting container is fixed in the spectacle frame, and the light-transmitting container has an enclosed accommodating space. The liquid storage chamber is arranged in the enclosed accommodating space of the light-transmitting container to store a liquid. The oscillator is installed on the liquid storage chamber to convert the liquid into fog stored in the enclosed accommodating space of the light-transmitting container.

20 Claims, 4 Drawing Sheets

MULTIFUNCTIONAL WEARING DEVICE

RELATED APPLICATIONS

This application claims priority to Taiwan Application Serial Number 112107334, filed Mar. 1, 2023, the disclosures of which are incorporated herein by reference in their entireties.

TECHNICAL FIELD

The present disclosure relates to a multifunctional wearing device. More particularly, the present disclosure relates to a multifunctional wearing device able to relax ciliary muscles of eyes.

BACKGROUND

When people use their eyes excessively and cause eye discomfort, people often hope to effectively remedy eye muscle fatigue, insufficient oxygen supply and other problems by changing the environment or external forces.

However, when the eyes look at objects at close range for a long time, the ciliary muscles will contract and tighten, so that the eyes will feel pressure. After the ciliary muscles contract and tighten for a long time, the ciliary muscles may become tight over time, resulting in soreness, numbness, pain, and tiredness.

Especially, when modern people stare at 3C products for a long time, it often causes ciliary muscle soreness, and the focusing function will also deteriorate, resulting in increased intraocular pressure and symptoms such as eye socket swelling and discomfort.

Therefore, there is a need to effectively reduce the pressure on the eyes so as to help people protecting their eyes, thereby extending the life of the eyes, and also help some patients with eye diseases or patients after eye surgery to relax the ciliary muscles thereof to reduce the stress on the eyes and eye fatigue, thereby protecting the eyes and increasing the life of the eyes.

SUMMARY

The summary of the present invention is intended to provide a simplified description of the disclosure to enable readers to have a basic understanding of the disclosure. The summary of the present invention is not a complete overview of the disclosure, and it is not intended to point out the importance of the embodiments/key elements of the present invention or define the scope of the invention.

One objective of the embodiments of the present invention is to provide a multifunctional wearing device able to achieve the effect of relaxing the ciliary muscles of the eyes by observing the cloud fog in an enclosed accommodating space.

To achieve these and other advantages and in accordance with the objective of the embodiments of the present invention, as the embodiment broadly describes herein, the embodiments of the present invention provides a multifunctional wearing device including a spectacle frame, a light-transmitting container, a liquid storage chamber and an oscillator. The light-transmitting container is fixed in the spectacle frame, and the light-transmitting container includes an enclosed accommodating space. The liquid storage chamber is disposed in the enclosed accommodating space of the light-transmitting container to store a liquid and the oscillator is installed on the liquid storage chamber to convert the liquid into a cloud fog. In addition, the cloud fog is stored in the enclosed accommodating space of the light-transmitting container.

In some embodiments, a light transmittance of the light-transmitting container is greater than 70%.

In some embodiments, the oscillator is an atomizing oscillator to produce a dry fog with a diameter of less than 10 micrometers (μm).

In some embodiments, the atomizing oscillator is a ceramic oscillator or an ultrasonic oscillator.

In some embodiments, the atomizing oscillator includes a capillary structure connected to a bottom of the atomizing oscillator.

In some embodiments, the multifunctional wearing device further includes a control circuit and a power supply. The control circuit is located in the spectacle frame, and the power supply is located in the spectacle frame and electrically connected to the control circuit and the oscillator to provide a required electrical power to the control circuit and the oscillator.

In some embodiments, the multifunctional wearing device further includes a fog density detector connected to the control circuit to detect a density of the cloud fog in the enclosed accommodating space, and the oscillator is turned on when the density of the cloud fog in the enclosed accommodating space is less than a fog level.

In some embodiments, the oscillator is turned off when the density of the cloud fog in the enclosed accommodating space is greater than a dense fog level.

In some embodiments, the multifunctional wearing device further includes a temperature sensor electrically connected to the control circuit to detect a temperature of the enclosed accommodating space.

In some embodiments, the multifunctional wearing device further includes a heater disposed in the enclosed accommodating space of the light-transmitting container and connected to the control circuit, and the heater heats the enclosed accommodating space of the light-transmitting container when the temperature sensor detect the temperature of the enclosed accommodating space is lower than a dew point.

In some embodiments, the heater is a positive temperature coefficient (PTC) heater.

In some embodiments, the PTC heater is a PTC ceramic heater.

In some embodiments, the multifunctional wearing device further includes a thermoelectric cooling chip disposed in the enclosed accommodating space of the light-transmitting container and connected to the control circuit to reduce the temperature of the enclosed accommodating space.

In some embodiments, the multifunctional wearing device further includes a transparent metal layer disposed on a surface of the light-transmitting container and connected to the heater and the thermoelectric cooling chip to increase or reduce a surface temperature of the light-transmitting container.

In some embodiments, the multifunctional wearing device further includes a forehead temperature measuring device connected to the control circuit to measure a forehead temperature of a user and record the forehead temperature of the user.

In some embodiments, the multifunctional wearing device further includes a blood oxygen saturation sensor detachably equipped on a spectacle temple of the spectacle frame to measure a blood oxygen saturation of a user and record the blood oxygen saturation of the user.

In some embodiments, the multifunctional wearing device further includes a plurality of fundus cameras installed on the spectacle frame and located around the light-transmitting container to take a fundus map and a cornea photo of a user.

In some embodiments, the multifunctional wearing device further includes a lighting device disposed on the spectacle frame to change a color of the cloud fog in the enclosed accommodating space of the light-transmitting container.

In some embodiments, the multifunctional wearing device further includes a fog exhaust hole located on the spectacle frame and aligned with the oscillator.

In some embodiments, the liquid storage chamber further includes a plurality of recycling holes.

Hence, after the oscillator of the multifunctional wearing device vibrates the liquid to convert the liquid into the cloud fog, the cloud fog can be discharged from the liquid storage chamber and stays in the enclosed accommodating space of the light-transmitting container. Therefore, the user may observe the cloud fog in the enclosed accommodating space to achieve the effect of relaxing the ciliary muscles of the eyes, thereby effectively curing the problems such as eye muscle fatigue and insufficient oxygen supply. Because the cloud fog only stays in the enclosed accommodating space and does not spray into the user's eyes so as to avoid the stinging of the user's eyes due to contact with water droplets and improve the overall user experience. In addition, since the cloud fog may stay in the enclosed accommodating space, the user can turn off the oscillator, instead of continuously running the oscillator to continuously generate cloud fog, so as to save an overall cost for generating the cloud fog with the multifunctional wearing device when the enclosed accommodating space is filled with cloud fog. Moreover, the multifunctional wearing device may occupy a small space and have a high degree of integration so as to conveniently carry and increase the convenience thereof.

BRIEF DESCRIPTION OF THE DRAWINGS

The disclosure can be more fully understood by reading the following detailed description of the embodiment, with reference made to the accompanying drawings as follows.

DETAILED DESCRIPTION OF THE PREFERRED EMBODIMENT

Figure 1:
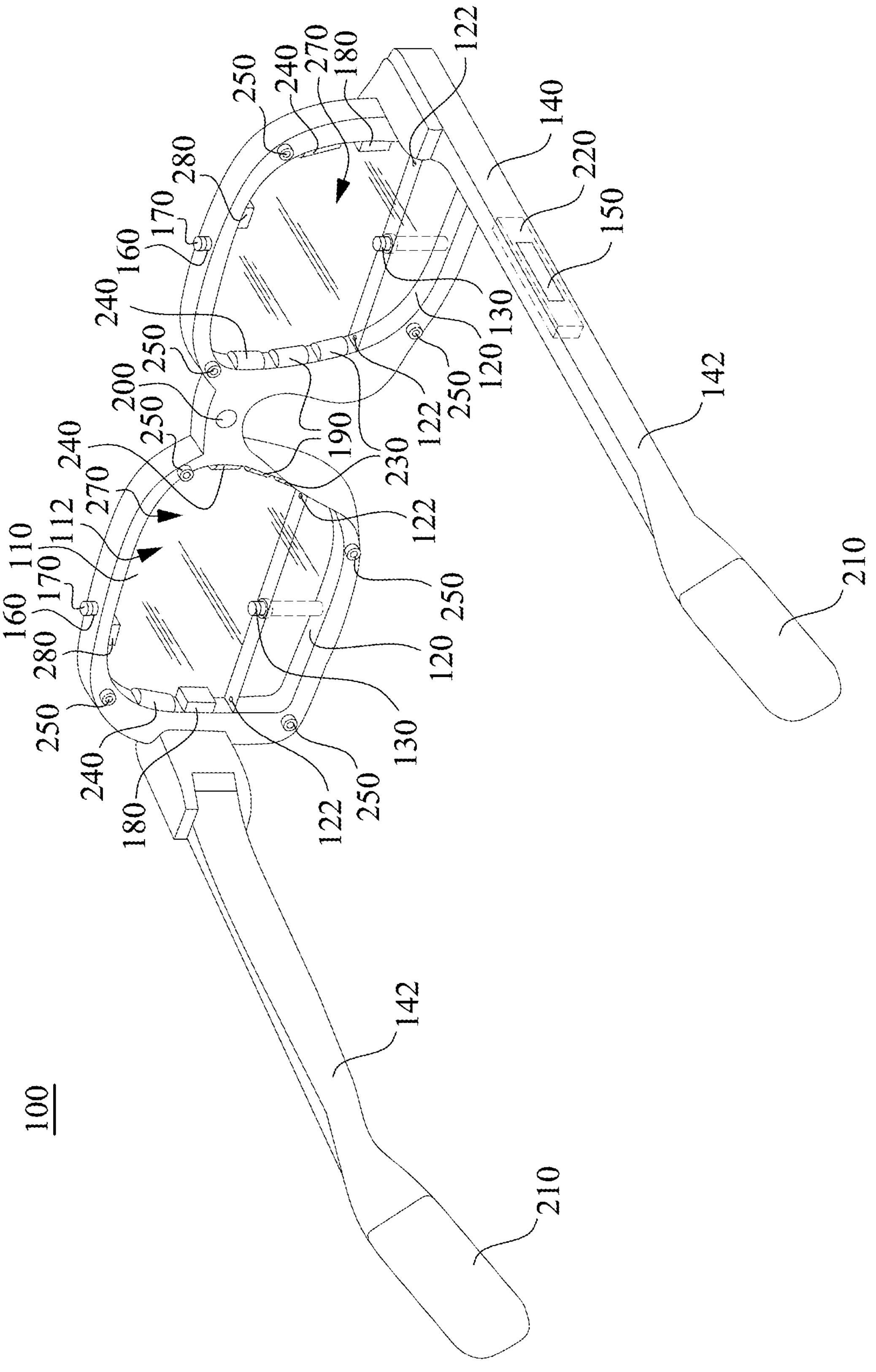
FIG. 1 illustrates a schematic perspective diagram of a multifunctional wearing device according to one embodiment of the present invention.

The following is a detailed description of the embodiments in conjunction with the accompanying drawings, but the provided embodiments are not intended to limit the scope of the disclosure, and the description of the structure and operation is not used to limit the execution sequence thereof. The structure of the recombination of components and the resulting devices with equal functions are all within the scope of this disclosure. In addition, the drawings are for illustration purposes only, and are not drawn according to the original scale. For ease of understanding, the same reference numbers are used in the drawings and the description to refer to the same or like parts.

In addition, the terms used in the entire description and the scope of the patent application, unless otherwise specified, usually have the usual meaning of each term used in this field, in the content disclosed here and in the special content. Some terms used to describe the disclosure are discussed below or elsewhere in this specification to provide additional guidance to those skilled in the art in the disclosure.

In the implementation mode and the scope of the present application, unless the article is specifically limited in the context, "a" and "the" can generally refer to a single or pluralities. In the steps, the numbering is only used to conveniently describe the steps, rather than to limit the sequence and implementation.

Secondly, the words "comprising", "including", "having", "containing" and the like used in the present application are all open language, meaning including but not limited to.

Figure 2:
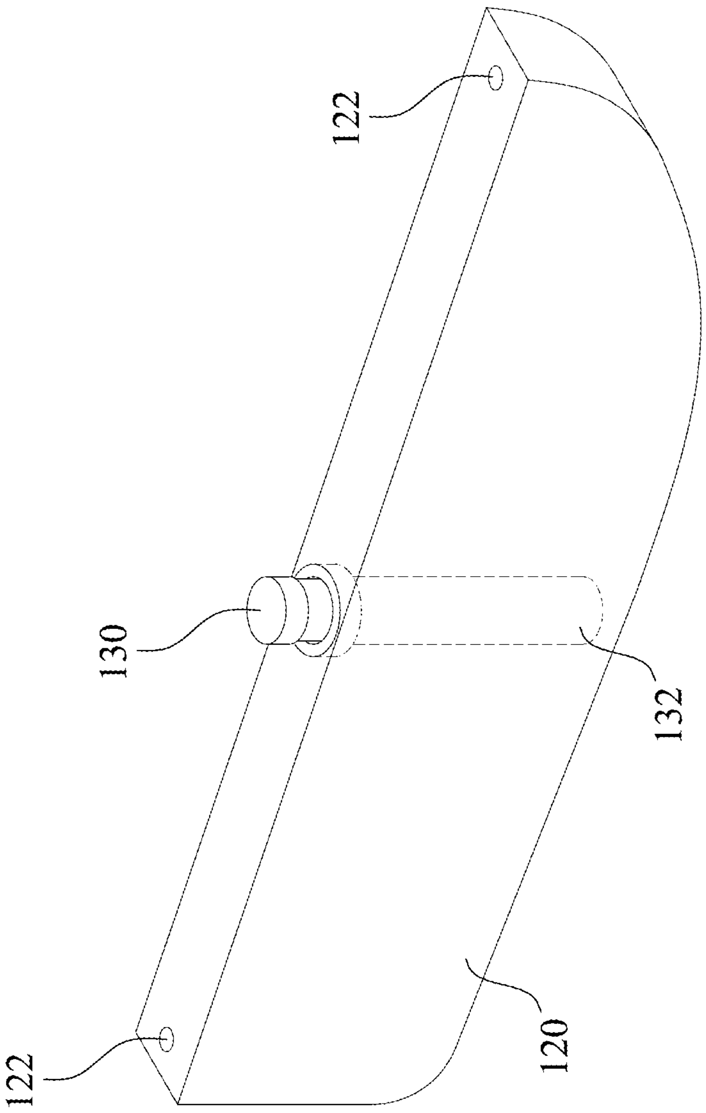
FIG. 2 illustrates a schematic perspective diagram of a liquid storage chamber equipped with an oscillator of the multifunctional wearing device of FIG. 1.

FIG. 1 illustrates a schematic perspective diagram of a multifunctional wearing device according to one embodiment of the present invention, and FIG. 2 illustrates a schematic perspective diagram of the liquid storage chamber equipped with the oscillator of the multifunctional wearing device of FIG. 1. The multifunctional wearing device 100 is, for example, a multifunctional glasses-type wearable device, but not limited thereto. In some embodiments, the multifunctional wearing device 100 includes a light-transmitting container 110, a liquid storage chamber 120, an oscillator 130 and a spectacle frame 140. The light-transmitting container 110 of the multifunctional wearing device 100 has an enclosed accommodating space 112. In some embodiments, the light-transmitting container 110 is fixed in the spectacle frame 140, and the light-transmitting container 110 may be a transparent lens and the enclosed accommodating space 112 of the light-transmitting container 110 may be hollow.

In some embodiments, a light transmittance of the light-transmitting container 110 is greater than 70%, preferably greater than 80%, and more preferably greater than 90%.

In some embodiments, the light-transmitting container 110 is made of a transparent material, preferably a transparent plastic material or glass material, such as glass, polyvinyl chloride (PVC), polymethacrylate (PMMA), polystyrene (PS), polyethylene terephthalate (PET), polycarbonate (PC), acrylonitrile-styrene copolymer (AS) or methyl methacrylate-styrene copolymer (MS; MMA Styrene Copolymer) and other materials, without departing from the spirit and protection scope of the present invention.

Therefore, a user may observe an object in the enclosed accommodating space 112 of the light-transmitting container 110. The liquid storage chamber 120 of the multifunctional wearing device 100 is located in the enclosed accommodating space 112 of the light-transmitting container 110, normally located at the bottom of the enclosed accommodating space 112, to store a required liquid inside the light-transmitting container 110.

In some embodiments, the liquid storage chamber 120 has recycling holes 122 to recycle the working liquid, e.g. water or any other liquid. Therefore, the liquid storage chamber 120 may store the liquid as well as retrieve the liquid with the liquid storage chamber 120 through the recycling holes 122 when the liquid is fallen in the enclosed accommodating space 112. Therefore, the user does not have to always replenish the liquid in the liquid storage chamber 120, and only when the liquid in the liquid storage chamber 120 is used up, the user needs to replenish the liquid again.

Figure 3:
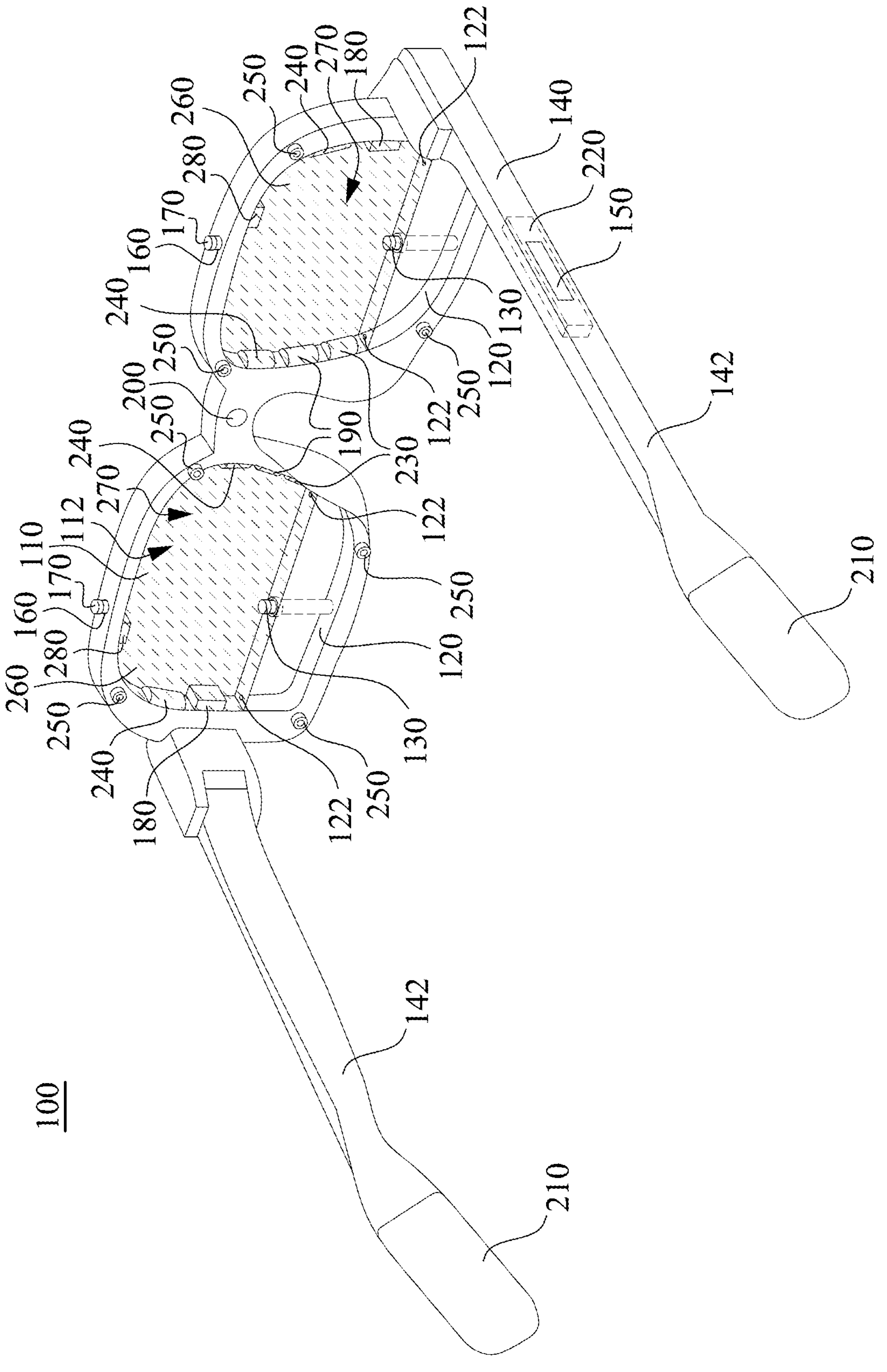
FIGS. 3 and 4 illustrate schematic diagrams of a multifunctional wearing device according to some embodiments of the present invention in use.

FIG. 3 illustrates a schematic diagram of the multifunctional wearing device 100 according to one embodiment of the present invention in use. In FIG. 3, the surface shading lines on the light-transmitting container 110 are omitted to clearly show the cloud fog 260 therein. Simultaneously referring to FIG. 2 and FIG. 3, the oscillator 130 of the multifunctional wearing device 100 is located on the liquid storage chamber 120. In some embodiments, the user may refill the liquid into the liquid storage chamber 120 so that the liquid storage chamber 120 is filled with liquid. Therefore, the oscillator 130 located in the liquid storage chamber 120 may be surrounded by the liquid to prevent the oscillation plate of the oscillator 130 from idling when the oscillation plate of the oscillator 130 is working but not in contact with the liquid.

The oscillator 130 may oscillate to convert the liquid in the liquid storage chamber 120 into the cloud fog 260 and the cloud fog 260 may enter into and stay in the enclosed accommodating space 112 of the light-transmitting container 110.

In some embodiments, the oscillator 130 further includes a capillary structure 132 connected the bottom of the atomizing oscillator 130 to utilize capillary action to transport the liquid stored in the liquid storage chamber 120 to the oscillator 130 so as to provide the required cloud fog 260.

In some embodiments, the oscillator 130 may be an atomizing oscillator 130 to produce the cloud fog 260, such as a dry fog having a diameter of less than 10 micrometers (μ) and preferably a dry fog having a diameter of about 5-10 μm.

Therefore, the light may be scattered by the cloud fog 260 in the enclosed accommodating space 112. Since the cloud fog 260 is a small water droplet, the cloud fog 260 may function as a convex lens so that the light reflected by the object cannot be correctly focused on the user's retina and may cause the object image to be blurry, thereby relaxing the ciliary muscles, and effectively improving the problems of eye muscle fatigue and insufficient oxygen supply of the eyes of the user.

In addition, since the cloud fog 260 stays in the enclosed accommodating space 112, the cloud fog 260 may not be sprayed into the user's eyes so as to avoid the stinging of the user's eyes due to contact with liquid droplets, thereby effectively improving the overall user experience.

Furthermore, because the cloud fog 260 may stay in the enclosed accommodating space 112, the user can manually or automatically turn off the oscillator 130, instead of continuously running the oscillator 130 to continuously generate cloud fog 260, so as to save an overall cost for generating the cloud fog 260 with the multifunctional wearing device 100 when the enclosed accommodating space 112 is filled with cloud fog 260. Moreover, the multifunctional wearing device 100 may occupy a small space and have a high degree of integration so as to conveniently carry and increase the convenience thereof.

In some embodiments, the multifunctional wearing device 100 further includes a control circuit 220 and a power supply 150 located in the spectacle frame 140. The power supply 150 is electrically connected to the control circuit 220 and the oscillator 130 to provide the required electrical powers for the control circuit 220 and the oscillator 130.

In some embodiments, one end of the control circuit 220 may be equipped with a universal serial bus (USB) connector, and the conductive wire of the power supply 150 is connected to the oscillator 130 so as to electrically connect to the oscillator 130. When the user uses the multifunctional wearing device 100, the required electrical power of the oscillator 130 may be provided by the power supply 150 equipped in the spectacle frame 140. After the user fill the liquid into the liquid storage chamber 120, the oscillator 130 may generate required cloud fog 260. In addition, the liquid of the oscillator 130 may be continuously supplied by way of the capillary structure 132 to prevent the oscillation plate of the oscillator 130 from not contacting the liquid and causing the oscillation plate to idle.

When the oscillator 130 vibrates, the liquid in the liquid storage chamber 120 is converted into the cloud fog 260 and the cloud fog 260 stays in the enclosed accommodating space 112 of the light-transmitting container 110.

In this way, the user may observe the cloud fog 260 in the enclosed accommodating space 112 to achieve the effect of relaxing the ciliary muscles of the eyes, thereby effectively curing the problems such as eye muscle fatigue and insufficient oxygen supply.

In some embodiments, the multifunctional wearing device 100 further includes a fog density detector 280 connected to the control circuit 220 to detect the density of the cloud fog 260 in the enclosed accommodating space 112. When the density of the cloud fog 260 in the enclosed accommodating space 112 is less than a fog level, for example, when a visual distance is about 200-500 meters, the oscillator 130 is turned on. When the density of the cloud fog 260 in the enclosed accommodating space 112 reaches a dense fog level, for example, when a visual distance is about 0-50 meters, the oscillator 130 may be turned off to save energy and improve the effective working time and service life of the multifunctional wearing device 100.

That is to say, when the density of the cloud fog 260 in the enclosed accommodating space 112 is between the fog level, the thick fog level and the dense fog level, for example, when the visual distance is about 50-500 meters, the oscillator 130 is turned on. When the density of the cloud fog 260 in the enclosed accommodating space 112 reaches a dense fog level, for example, when a visual distance is less than 50 meters, the oscillator 130 may be turned off or intermittently turned off to adjust the density of the cloud fog 260 in the enclosed accommodating space 112, and when the cloud fog 260 makes the visual distance higher than 500 meters, the oscillator 130 continues to work to increase the density of the cloud fog 260, but not limited thereto.

In some embodiments, the fog density detector 280 of the multifunctional wearing device 100 is a visibility meter.

In some embodiments, the oscillator 130 may be a ceramic oscillator or an ultrasonic oscillator. For example, the ceramic oscillator can generate a piezoelectric effect through a current circuit and therefore generate mechanical vibration on the oscillation plate of the ceramic oscillator. At the time, the ceramic oscillator may transfer the vibration generated by the oscillation plate to the liquid, such as water, and cause the liquid water to atomize to produce cloud fog 260. On the other hand, the ultrasonic oscillator uses electronic high-frequency oscillation (oscillation frequency is about 1.7 MHz) to perform high-frequency resonance on the oscillation plate of the ultrasonic oscillator to break up the liquid water molecule structure around the oscillation plate to generate sufficient density of the cloud fog 260 in the enclosed accommodating space 112.

It is worth noting that the enclosed accommodating space 112 of the light-transmitting container 110 is hollow to allow the user observing the cloud fog 260 in the enclosed accommodating space 112 of the light-transmitting container 110. The user may achieve the effect of relaxing the ciliary muscles of the eyes by observing the cloud fog 260 in the enclosed accommodating space 112, thereby dilating the pupils and effectively curing problems such as eye muscle fatigue and insufficient oxygen supply. Because the cloud fog 260 only stays in the enclosed accommodating space 112 and does not spray into the user's eyes so as to avoid the stinging of the user's eyes due to contact with water droplets and improve the overall user experience. In addition, the multifunctional wearing device 100 occupies a small space and has a high degree of integration so as to conveniently carry and increase the convenience thereof.

In some embodiments, the multifunctional wearing device 100 further includes a temperature sensor 230 electrically connected to the control circuit 220, and the temperature sensor 230 is disposed in the enclosed accommodating space 112 to measure the temperature in the enclosed accommodating space 112.

In some embodiments, the multifunctional wearing device 100 further includes a heater 180 disposed in the enclosed accommodating space 112 of the light-transmitting container 110 and electrically connected to the control circuit 220. When the temperature in the enclosed accommodating space 112 measured by the temperature sensor 230 is lower than a dew point, the control circuit 220 may turn on the heater 180 to increase the temperature of the enclosed accommodating space 112 of the light-transmitting container 110 so as to effectively prevent cloud fog 260 from forming water droplets.

In some embodiments, the heater 180 may be a positive temperature coefficient (PTC) heater, such as a PTC ceramic heater having the advantages of high heating efficiency, power saving, automatic constant temperature, high safety and long service life. In addition, while the PTC ceramic heater is in direct contact with paper or cloth, the paper or cloth may not catch fire to effectively improve the safety of the multifunctional wearing device 100.

In some embodiments, the multifunctional wearing device 100 further includes a thermoelectric cooling chip 190 disposed in the enclosed accommodating space 112 of the light-transmitting container 110 and connected to the control circuit 220 to reduce and control the temperature in the enclosed accommodating space 112.

In some embodiments, the multifunctional wearing device 100 further includes a transparent metal layer 270 formed on the surface of the light-transmitting container 110 and connected to the heater 180 and the thermoelectric cooling chip 190 to transfer the heat generated by the heater 180 to the surface of the light-transmitting container 110 and remove too much heat on the surface of the light-transmitting container 110 by the thermoelectric cooling chip 190 to reduce the temperature of the light-transmitting container 110 so as to uniformly increase or reduce the surface temperature of the light-transmitting container 110.

In some embodiments, the multifunctional wearing device 100 further includes a forehead temperature measuring device 200 connected to the control circuit 220 and disposed in a center position of the spectacle frame 140 to measure a user forehead temperature and record the measured temperature data to store body temperature changes of the user when the user wears the multifunctional wearing device 100.

In some embodiments, the forehead temperature measuring device 200 may be an infrared forehead temperature measuring device.

In some embodiments, the multifunctional wearing device 100 further includes a blood oxygen saturation sensor 210 detachably equipped on the terminal of the spectacle temple 142 of the spectacle frame 140 to measure a blood oxygen saturation value of a user and record the measured blood oxygen saturation value to store blood oxygen saturation changes of the user when the user wears the multifunctional wearing device 100.

In some embodiments, the multifunctional wearing device 100 further includes a plurality of fundus cameras 250 installed on the spectacle frame 140 and located around the light-transmitting container 110 to take fundus maps and cornea photos of a user. Therefore, when the user uses the multifunctional wearing device 100, the cloud fog 260 may be used to effectively relax the ciliary muscles of the eyes and dilate the pupils. At this time, the user can take fundus maps and cornea photos without using chemical agents, such as mydriatic drug (also known as ciliary muscle relaxant) to dilate the pupil so as to reduce the risk of the user dependence on chemicals as well as effectively relax the ciliary muscle and eliminate ciliary muscle tightness.

In some embodiments, the multifunctional wearing device 100 further includes a lighting device 240 disposed on the spectacle frame 140 to change the color of the cloud fog 260 in the enclosed accommodating space 112 of the light-transmitting container 110. The lighting device 240 is, for example, light-emitting diodes, and preferably color light-emitting diodes, to reduce eye fatigue with appropriate spectrum, such as green light.

Figure 4:
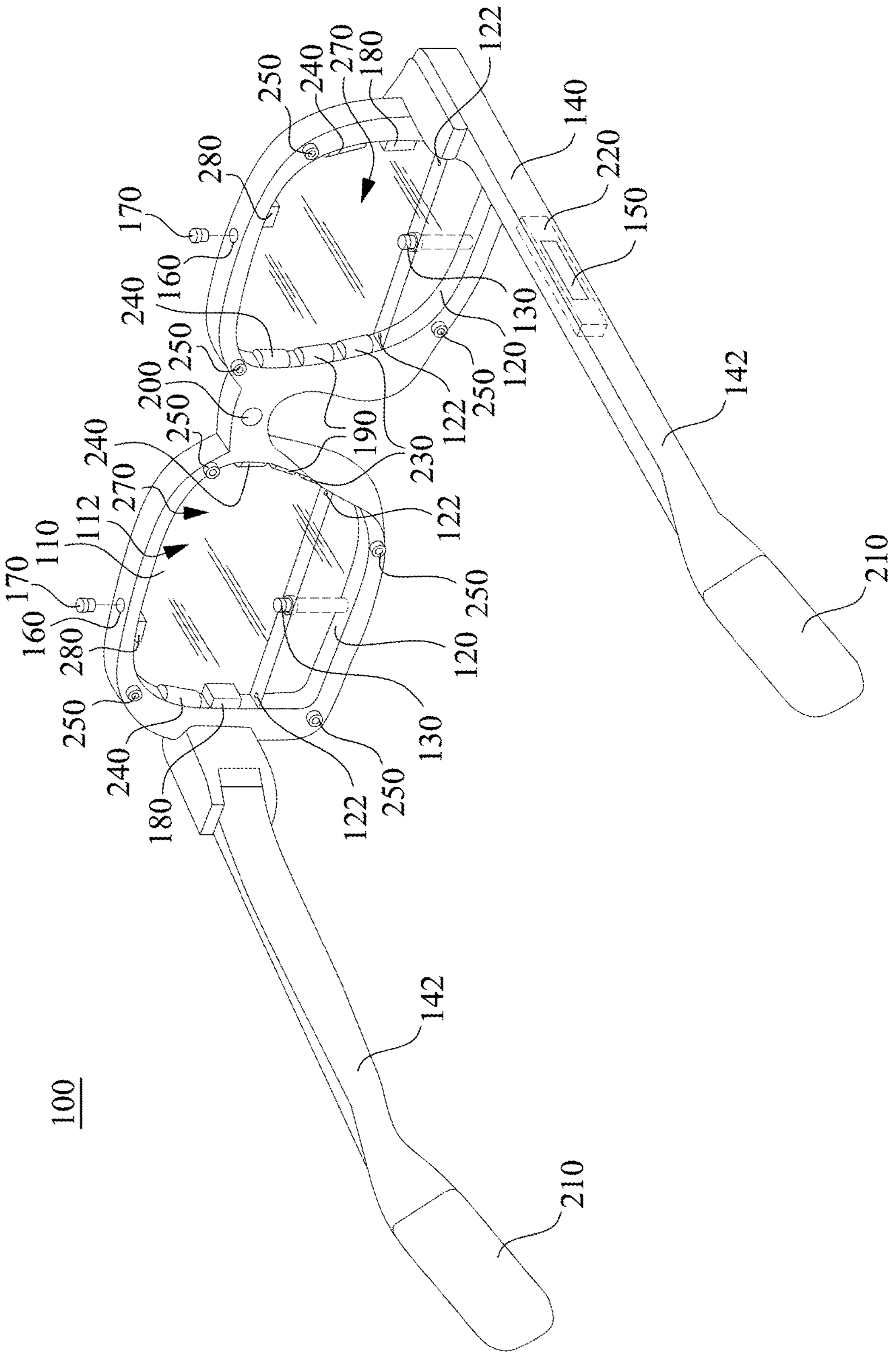

Further referring to FIG. 4, a multifunctional wearing device 100 according to some embodiments of the present invention in use is illustrated. Simultaneously referring to FIG. 3 and FIG. 4, the multifunctional wearing device 100 further includes a fog exhaust hole 160 and a blocking plug 170. Preferably, the fog exhaust hole 160 is aligned with the oscillator 130 below. The fog exhaust hole 160 of the multifunctional wearing device 100 is located on the spectacle frame 140 and the blocking plug 170 is engaged with the fog exhaust hole 160. When the oscillator 130 vibrates to convert the liquid in the liquid storage chamber 120 into cloud fog 260, the cloud fog 260 is discharged from the liquid storage chamber 120 and stays in the enclosed accommodating space 112 of the light-transmitting container 110. The user may observe the cloud fog 260 in the enclosed accommodating space 112 to achieve the effect of relaxing the ciliary muscles of the eyes, thereby effectively curing the problems such as eye muscle fatigue and insufficient oxygen supply.

In some embodiments, after using the multifunctional wearing device 100, the blocking plug 170 may be pulled out from the fog exhaust hole 160 so that the cloud fog 260 is discharged from the enclosed accommodating space 112 through the fog exhaust hole 160 and diffused into the environment. In this way, the multifunctional wearing device 100 may avoid that the cloud fog 260 stays in the enclosed accommodating space 112 for a long time so as to avoid bacterial growth. Therefore, such a configuration may effectively improve the use environment of the multifunctional wearing device 100. In addition, the multifunctional wearing device 100 only needs to occupy a small space and has a high degree of integration. The user may conveniently carry the multifunctional wearing device 100 so as to increase the convenience thereof and the user willingness to use the multifunctional wearing device 100.

Accordingly, after the oscillator 130 of the multifunctional wearing device 100 vibrates the liquid to convert the liquid into the cloud fog 260, the cloud fog 260 can be discharged from the liquid storage chamber 120 and stays in the enclosed accommodating space 112 of the light-transmitting container 110. Therefore, the user may observe the cloud fog 260 in the enclosed accommodating space 112 to achieve the effect of relaxing the ciliary muscles of the eyes, thereby effectively curing the problems such as eye muscle fatigue and insufficient oxygen supply. Because the cloud fog 260 only stays in the enclosed accommodating space 112 and does not spray into the user's eyes so as to avoid the stinging of the user's eyes due to contact with water droplets and improve the overall user experience. In addition, since the cloud fog 260 may stay in the enclosed accommodating space 112, the user can turn off the oscillator 130, instead of continuously running the oscillator 130 to continuously generate cloud fog 260, so as to save an overall cost for generating the cloud fog 260 with the multifunctional wearing device 100 when the enclosed accommodating space 112 is filled with cloud fog 260. Moreover, the multifunctional wearing device 100 may occupy a small space and have a high degree of integration so as to conveniently carry and increase the convenience thereof.

Although the present disclosure has been disclosed above in terms of implementation, it is not intended to limit the present disclosure. Any person with ordinary knowledge in the field may make various variations and modifications without departing from the spirit and scope of the disclosure. Therefore, the spirit and scope of the appended claims should not be limited to the description of the embodiments contained herein.

What is claimed is:

1. A multifunctional wearing device, comprising:

a spectacle frame;

a light-transmitting container fixed in the spectacle frame, wherein the light-transmitting container comprises an enclosed accommodating space;

a liquid storage chamber disposed in the enclosed accommodating space of the light-transmitting container to store a liquid; and an oscillator installed on the liquid storage chamber to convert the liquid into a cloud fog, wherein the cloud fog is stored in the enclosed accommodating space of the light-transmitting container.

2. The multifunctional wearing device of claim 1, wherein a light transmittance of the light-transmitting container is greater than 70%.

3. The multifunctional wearing device of claim 1, wherein the oscillator is an atomizing oscillator to produce a dry fog with a diameter of less than 10 micrometers (μm).

4. The multifunctional wearing device of claim 3, wherein the atomizing oscillator is a ceramic oscillator or an ultrasonic oscillator.

5. The multifunctional wearing device of claim 3, wherein the atomizing oscillator comprises a capillary structure connected to a bottom of the atomizing oscillator.

6. The multifunctional wearing device of claim 5, further comprising:

a control circuit located in the spectacle frame; and a power supply located in the spectacle frame and electrically connected to the control circuit and the oscillator to provide a required electrical power to the control circuit and the oscillator.

7. The multifunctional wearing device of claim 6, further comprising:

a fog density detector connected to the control circuit to detect a density of the cloud fog in the enclosed accommodating space, wherein the oscillator is turned on when the density of the cloud fog in the enclosed accommodating space is less than a fog level.

8. The multifunctional wearing device of claim 7, wherein the oscillator is turned off when the density of the cloud fog in the enclosed accommodating space is greater than a dense fog level.

9. The multifunctional wearing device of claim 6, further comprising:

a temperature sensor electrically connected to the control circuit to detect a temperature of the enclosed accommodating space.

10. The multifunctional wearing device of claim 9, further comprising:

a heater disposed in the enclosed accommodating space of the light-transmitting container and connected to the control circuit, wherein the heater heats the enclosed accommodating space of the light-transmitting container when the temperature sensor detect the temperature of the enclosed accommodating space is lower than a dew point.

11. The multifunctional wearing device of claim 10, wherein the heater is a positive temperature coefficient (PTC) heater.

12. The multifunctional wearing device of claim 11, wherein the PTC heater is a PTC ceramic heater.

13. The multifunctional wearing device of claim 10, further comprising:

a thermoelectric cooling chip disposed in the enclosed accommodating space of the light-transmitting container and connected to the control circuit to reduce the temperature of the enclosed accommodating space.

14. The multifunctional wearing device of claim 13, further comprising:

a transparent metal layer disposed on a surface of the light-transmitting container and connected to the heater and the thermoelectric cooling chip to increase or reduce a surface temperature of the light-transmitting container.

15. The multifunctional wearing device of claim 6, further comprising:

a forehead temperature measuring device connected to the control circuit to measure a forehead temperature of a user and record the forehead temperature of the user.

16. The multifunctional wearing device of claim 6, further comprising:

a blood oxygen saturation sensor detachably equipped on a spectacle temple of the spectacle frame to measure a blood oxygen saturation of a user and record the blood oxygen saturation of the user.

17. The multifunctional wearing device of claim 6, further comprising:

a plurality of fundus cameras installed on the spectacle frame and located around the light-transmitting container to take a fundus map and a cornea photo of a user.

18. The multifunctional wearing device of claim 6, further comprising:

a lighting device disposed on the spectacle frame to change a color of the cloud fog in the enclosed accommodating space of the light-transmitting container.

19. The multifunctional wearing device of claim 1, further comprising:

a fog exhaust hole located on the spectacle frame and aligned with the oscillator.

20. The multifunctional wearing device of claim 1, wherein the liquid storage chamber further comprises a plurality of recycling holes.

* * * * *